(12) United States Patent
Devine et al.

(10) Patent No.: US 8,309,067 B2
(45) Date of Patent: *Nov. 13, 2012

(54) HAIR STRAIGHTENING COMPOSITION COMPRISING A DISACCHARIDE

(75) Inventors: Karen Maria Devine, Wirral (GB); Richard Skinner, Wirral (GB); Cheryl Anne Taylor, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 652 days.

This patent is subject to a terminal disclaimer.

(21) Appl. No.: 12/086,091

(22) PCT Filed: Nov. 6, 2006

(86) PCT No.: PCT/EP2006/010713
§ 371 (c)(1),
(2), (4) Date: Jun. 5, 2008

(87) PCT Pub. No.: WO2007/065521
PCT Pub. Date: Jun. 14, 2007

(65) Prior Publication Data
US 2009/0142288 A1 Jun. 4, 2009

(30) Foreign Application Priority Data
Dec. 7, 2005 (EP) ..................... 05257520

(51) Int. Cl.
*A61Q 5/04* (2006.01)
(52) U.S. Cl. .................................. 424/70.2
(58) Field of Classification Search .................. 424/70.2
See application file for complete search history.

(56) References Cited

U.S. PATENT DOCUMENTS

| | | | |
|---|---|---|---|
| 3,628,910 A * | 12/1971 | Grayson | 8/127.51 |
| 4,685,931 A * | 8/1987 | Schieferstein et al. | 8/406 |
| 4,855,130 A | 8/1989 | Konrad et al. | 424/70 |
| 4,947,878 A | 8/1990 | Crews et al. | 132/203 |
| 5,415,856 A * | 5/1995 | Crews et al. | 424/70.2 |
| 5,639,449 A | 6/1997 | Syed et al. | 424/70.17 |
| 5,641,477 A | 6/1997 | Syed et al. | 424/70.4 |
| 6,506,501 B1 | 1/2003 | Schonert et al. | 428/537.5 |
| 7,078,025 B2 * | 7/2006 | Kripp et al. | 424/70.2 |
| 2002/0189027 A1 * | 12/2002 | Cannell et al. | 8/405 |
| 2003/0099605 A1 * | 5/2003 | Browning | 424/70.2 |

FOREIGN PATENT DOCUMENTS

| | | |
|---|---|---|
| DE | 36 02 746 | 8/1987 |
| DE | 101 05 922 | 8/2002 |
| DE | 101 46 350 | 4/2003 |
| DE | 101 63 860 | 7/2003 |
| EP | 1 362 573 | 11/2003 |
| JP | 2004 26770 | 1/2004 |
| JP | 2004210700 A * | 7/2004 |
| JP | 2004 256410 | 9/2004 |
| WO | 99/29282 | 6/1999 |
| WO | 01/68040 | 9/2001 |
| WO | WO 2004052526 A1 * | 6/2004 |
| WO | WO 2004054526 A1 * | 7/2004 |

OTHER PUBLICATIONS

Wikipedia, Sodium Hydroxide [Downloaded Jun. 29, 2011] [Retrieved from internet <URL: http://en.wikipedia.org/wiki/Sodium_Hydroxide >], 10 pages.*
Merriam-Webster Disctionary [Downloaded Jun. 29, 2011] [Retrieved from internet <URL: http://www.merriam-webster.com/dictionary/aqueous >], 2 pages.*
Kazuki, JP 2004 026770, partial translation (Tables 1-3, 6-7) by Irina Knizhnik (USPTO), Dec. 12, 2011, 2 pages.*
PCT International Search Report in PCT application PCT/EP2006/010713.
Derwent Abstract of DE 101 05 922—published Aug. 22, 2002.
Derwent Abstract of DE 101 63 860—published Jul. 10, 2003.

* cited by examiner

*Primary Examiner* — Tracy Vivlemore
*Assistant Examiner* — Miriam A Levin
(74) *Attorney, Agent, or Firm* — Ronald A. Koatz

(57) ABSTRACT

A hair straightening composition comprising at least one hydroxide ion generator and a disaccharide.

8 Claims, No Drawings

HAIR STRAIGHTENING COMPOSITION COMPRISING A DISACCHARIDE

This application is a National Stage application of PCT/EP2006/010713, filed Nov. 6, 2006 and claims priority to application EP 05257520, filed Dec. 7, 2005, the entire disclosures of which are incorporated herein by reference.

FIELD OF THE INVENTION

The present invention relates to compositions for straightening hair.

BACKGROUND AND PRIOR ART

Straightening or relaxing the curls of very curly hair is thought to increase the manageability and ease of styling of such hair. There is an increasing demand for the hair care products referred to as "hair relaxers," which can relax or straighten naturally curly or kinky hair. Hair relaxers may either be applied in a hair salon by a professional or in the home by the individual consumer.

U.S. Pat. No. 4,947,878 discloses formulations for treating hair comprising cysteine and a non-reducing disaccharide. U.S. Pat. No. 5,641,477 discloses a process for reducing damage to hair by applying to the hair a composition comprising sodium hydroxide and sucrose.

Hair fibre, a keratinous material, comprises proteins (polypeptides). Many of the polypeptides in hair fibers are bonded together or cross-linked with disulfide bonds (—S—S—). A disulfide bond may be formed from the reaction of two sulfhydryl groups (—SH), one on each of two cysteine residues, which results in the formation of a cystine residue. A cystine residue comprises a cross-link of the formula —CH2-S—S—CH2- between 2 polypeptides.

While there are other types of bonds which occur between the polypeptides in hair fibres, such as ionic (salt) bonds, the permanent curling or the shape of the hair is essentially dependent on the disulfide bonds of cystine residues.

As a result, relaxing or straightening of hair can be achieved by disrupting the disulfide bonds of the hair fibres with an alkaline agent or a −2 reducing agent. The chemical disruption of disulfide bonds by an alkaline agent is usually combined with mechanical straightening of the hair, such as combing, and straightening generally occurs due to changes of the relative positions of opposite polypeptide chains within the hair fibre. The reaction is generally terminated by rinsing and/or the application of a neutralizing composition. The reaction with the alkaline agent is normally initiated by hydroxide ions.

Specifically, hydroxide ions initiate a reaction in which a cystine cross-link (—CH2-S—S—CH2-) is broken and a lanthionine cross-link (—CH2-S—CH2-) is formed.

Consequently, the term "lanthionizing" is used when one skilled in the art refers to the relaxing or straightening of keratin fibres by hydroxide ions.

Hair that has been lanthionized using hydroxide ion generating compositions frequently feels harsh and can to break during grooming.

Thus, there is still a need for compositions and methods to relax keratin fibres which preserve the relaxing efficiency of hydroxide ion yet do not cause the negative attributes associated with lanthionized hair.

DESCRIPTION OF THE INVENTION

The present invention, in one aspect, provides a hair straightening composition having a pH from 12 to 14 comprising at least one hydroxide ion generator and a disaccharide selected from the group consisting of trehalose, cellobiose or mixtures thereof.

In another aspect of the invention, there is provided a method for straightening hair comprising applying to the hair a composition described above.

A further aspect of this invention is the use of trehalose, cellobiose or mixtures thereof in a hydroxide based straightening system to mitigate hair damage.

DETAILED DESCRIPTION OF THE INVENTION

The Disaccharide

The present invention comprises as an essential element of the invention a disaccharide, selected from the group consisting of trehalose, cellobiose or mixtures thereof.

Disaccharides can be either reducing or non-reducing sugars. Non-reducing sugars are preferred.

The D(+) form of the sugars are preferred. Trehalose is the most preferred disaccharide.

The level of disaccharides present in the total formulation is from 0.05 wt % to 49 wt %, more preferably from 0.2 wt % to 3 wt %, most preferably from 0.5 wt % to 2 wt %.

Hydroxide Ion Generator

In the context of the present invention "hydroxide ion generator" refers to both compounds and compositions that generate hydroxide ions, and compounds and compositions that comprise hydroxide ions. For example, in one embodiment, the relaxing composition comprises at least one hydroxide ion generator which generates hydroxide ions in situ. Hydroxide ion generators may, for example, be chosen from traditional "lye" and "no lye" hair relaxer compositions and other soluble or slightly soluble hydroxide ion sources.

Further, the at least one hydroxide ion generator may be used in combination chelating agents, sequestering agents, and salts thereof.

Sodium hydroxide is the preferred hydroxide ion generator.

Preferably the hydroxide generator is present in the composition at levels from 0.1 to 10 Wt %, preferably from 0.5 to 5 wt %. These levels apply whether the hydroxide is present in the same composition as the disaccharide or in a separate composition.

The ratio of hydroxide ion generator to disaccharide is preferably from 3:1 to 3:2.

Di-Acids

Di-acids are preferably present in the compositions of the present invention, particularly suitable are di-acids having the formula:

$$\text{HOOC—(CH}_2)_n\text{—COOH}$$

where n is an integer from 2 to 8, more preferably where n is equal to 2 or 4 (succinic acid and adipic acid respectively).

The acids may be present as a salt.

Organic acids are best used at levels in the total formulation from 0.01 wt % to 5 wt %, more preferably at levels from 0.1 wt % to 2 wt %.

The weight ratio of di-acid to disaccharide is preferably from 1:10 to 20:1, more preferably 1:4 to 4:1.

Guanidinium Salt

Optionally a guanidinium salt is present. For example, guanidinium carbonate, guanidinium sulphate and guanidinium phosphate. Particularly preferred is guanidinium carbonate. Guanidinium salts are best used at levels from 0.01 wt % w to 5 wt. % of the total formulation, more preferably at 0.1 wt % w to 2 wt %.

The preferred weight ratio of guanidinium salt to disaccharide is from 1:10 to 20:1, more preferably from 1:4 to 4:1.

In addition the preferred guanidinium salt:disaccharide molar ratios are from 0.1:1 to 10:1, more preferably from 0.1:1 to 2:1.

The Alkali Metal Salt

The composition may comprise an alkali metal salt, preferably the alkali metal salt is a sulphate, more preferably it is sodium sulphate.

As an alternative to the above the salt may be a carbonate, particularly preferred is ammonium carbonate.

The alkali metal salt is present at a level from 0.001 wt % of the total composition, preferably from 0.05 wt %, most preferably from 0.1 wt %. The maximum level of salt is preferably less than 20 wt %.

The preferred product form is a cream.

In one aspect the product is in the form of a kit consisting of two parts. The first part comprises the hydroxide components and is preferably formulated as a cream. The second part comprises the disaccharide and may be in a liquid or solid form. The disaccharide could be used either as neat active or as a diluted slurry, dispersion or solution. The two parts of the kit are mixed immediately before application to the hair. In the context of this invention the term "immediately before application" means approximately 5 minutes or less before application.

It is preferable if in addition to the disaccharide the second composition comprises any one of a guanidinium salt, di-acid or sulphate based salt or mixtures thereof. Those species that are listed as preferred above are also preferred in this kit form.

Other Constituents

Other constituents, which can be used in the compositions of the invention can be chosen from solvents such as alcohol and water; preservatives; perfumes; UV filters; active hair care agents; plasticizers; anionic, cationic, amphoteric, non-ionic, and zwitterionic surfactants; hair conditioning agents such as silicone fluids, fatty esters, fatty alcohol, fatty chain hydrocarbons, emollients, lubricants, and penetrants such as lanolin compounds, protein hydrolysates, and other protein derivatives; anionic, cationic, amphoteric, nonionic, and zwitterionic polymers; dyes; tints; bleaches; reducing agents; pH adjusting agents; sunscreens; and thickening agents.

Products of the invention may further comprise organic nucleophiles chosen from basic amino acids such as lysine, amines, alcohols and mercaptans and derivatives thereof.

The invention will now be illustrated by the following non-limiting Examples. Examples of the invention are illustrated by a number, comparative examples are illustrated by a letter.

TABLE 1

Relaxer Formulation With Hydroxide + Disaccharide

| Ingredient | wt/% | | |
|---|---|---|---|
| | Example A | Example B | Example 1 |
| Pet Jelly | 15 | 15 | 15 |
| Mineral Oil | 20 | 20 | 20 |
| Polawax GP200 | 3 | 3 | 3 |
| Laurex CS | 4 | 4 | 4 |
| EDTA Sodium | 0.1 | 0.1 | 0.1 |
| Tween 60 | 2 | 2 | 2 |

TABLE 1-continued

Relaxer Formulation With Hydroxide + Disaccharide

| Ingredient | wt/% | | |
|---|---|---|---|
| | Example A | Example B | Example 1 |
| Solan E Pellets | 0.625 | 0.625 | 0.625 |
| Propylene Glycol | 5 | 5 | 5 |
| NaOH | 2 | 2 | 2 |
| Trehalose | 0 | 0 | 0.8 |
| Adipic Acid | 0 | 0 | 0.2 |
| Guanidine Carbonate | 0 | 0.2 | 0.2 |
| Water | to 100 | to 100 | to 100 |

Hair switches of identical hair type were treated with the above compositions under ambient conditions for 30 minutes. Each switch was then rinsed, shampooed, rinsed and allowed to dry naturally for 18 hours. Each switch was trimmed to a length of 20 cm. The switches were then analysed by a trained sensory panel using the Paired Comparison Bradley Terry Analysis.

| Treatment | Smoothness Preference | Softness Preference |
|---|---|---|
| Example 1 | 50% | 56% |
| Example A | 23% | 18% |
| Example B | 26% | 25% |

It can thus be seen that the Example of the invention gave better preference scores than the comparative Examples.

The invention claimed is:

1. A hair straightening composition having a pH from 12 to 14 and comprising i) at least one hydroxide ion generator which generates hydroxide ions in situ in an amount to provide pH of 12-14 and which is sodium hydroxide, ii) a disaccharide selected from trehalose, cellobiose or mixtures thereof; and iii) a diacid, wherein the ratio of hydroxide ion generator to disaccharide is 3:1 to 3:2.

2. A hair straightening composition according to claim 1 in which the disaccharide is a trehalose.

3. A hair treatment composition according to claim 2 in which the di-acid has the formula:

HOOC—(CH$_2$)$_n$—COOH

Where n is an integer from 2 to 8.

4. A hair treatment composition according to claim 3 where n is equal to 2 or 4.

5. A hair treatment composition according to claim 1, which further comprises a guanidinium salt.

6. A hair treatment composition according to claim 5 in which the guanidinium salt is a carbonate.

7. A method for lanthionizing keratin fibres to achieve relaxation of said keratin fibres in which a composition according to claim 1 is applied to the hair.

8. A method of mitigating hair damage by applying to hair a composition according to claim 1.

* * * * *